United States Patent
Gurge et al.

(10) Patent No.: US 8,623,330 B2
(45) Date of Patent: Jan. 7, 2014

(54) EMOLLIENT FOAMS FOR TREATMENT OF SEBORRHEIC DERMATITIS

(75) Inventors: Ronald M. Gurge, Franklin, MA (US); Mark W. Trumbore, Westford, MA (US); Wendy Schilling, Warwick, RI (US); Lisa Chin, Narragansett, RI (US)

(73) Assignee: Precision Dermatology, Inc., Cumberland, RI (US)

( * ) Notice: Subject to any disclaimer, the term of this patent is extended or adjusted under 35 U.S.C. 154(b) by 291 days.

(21) Appl. No.: 13/017,204

(22) Filed: Jan. 31, 2011

(65) Prior Publication Data

US 2011/0229417 A1 Sep. 22, 2011

Related U.S. Application Data

(60) Provisional application No. 61/315,101, filed on Mar. 18, 2010.

(51) Int. Cl.
*A61K 9/00* (2006.01)
*A61K 9/107* (2006.01)
*A61K 9/12* (2006.01)

(52) U.S. Cl.
USPC .............................. 424/45; 514/865; 514/945

(58) Field of Classification Search
USPC ..................................... 424/45; 514/864, 945
See application file for complete search history.

(56) References Cited

U.S. PATENT DOCUMENTS

| | | | |
|---|---|---|---|
| 4,695,451 A | 9/1987 | Straw et al. | |
| 4,806,262 A | 2/1989 | Snyder | |
| 5,658,559 A * | 8/1997 | Smith | 424/78.02 |
| 2004/0202618 A1 * | 10/2004 | Riedel et al. | 424/47 |
| 2005/0042182 A1 * | 2/2005 | Arkin et al. | 424/47 |
| 2005/0069566 A1 | 3/2005 | Tamarkin et al. | |
| 2006/0233721 A1 | 10/2006 | Tamarkin et al. | |
| 2007/0036731 A1 | 2/2007 | Hirsh et al. | |
| 2007/0098647 A1 | 5/2007 | Neubourg | |
| 2007/0154402 A1 | 7/2007 | Trumbore et al. | |
| 2008/0206161 A1 * | 8/2008 | Tamarkin et al. | 424/45 |
| 2009/0017147 A1 * | 1/2009 | Lintner et al. | 424/780 |
| 2009/0233892 A1 * | 9/2009 | Sen et al. | 514/179 |
| 2009/0257957 A1 * | 10/2009 | Burnier et al. | 424/45 |
| 2010/0284948 A1 * | 11/2010 | Ohrmann et al. | 424/59 |
| 2011/0305643 A1 * | 12/2011 | Gurge et al. | 424/45 |

OTHER PUBLICATIONS

Johnson et al. "Treatment of Seborrheic Dermatitis," Am. Fam. Physician May 1, 2000, 61(9), pp. 2703-2710, accessed at http://www.aafp.org/afp/2000/0501/p2703.html?printable=afp on May 11, 2013 and printed as pp. 1-14.*
International Search Report dated Oct. 12, 2011 from PCT/US2011/023178.

* cited by examiner

*Primary Examiner* — James H. Alstrum-Acevedo
(74) *Attorney, Agent, or Firm* — Foley Hoag LLP

(57) ABSTRACT

Described herein are emulsions and compositions for the treatment of various dermatoses. The emulsions may be formulated as aerosol compositions. The aerosol propellant may be a hydrofluoroalkane propellant. Also described are methods of treating dermatoses, comprising the step of applying to an affected area of a subject in need thereof a therapeutically-effective amount of an inventive emulsion or aerosol composition. The dermatosis may be seborrheic dermatitis.

8 Claims, 5 Drawing Sheets

Figure 1

| Component (%) | NB298-54A | NB298-54B | NB298-54C | NB298-54E | NB298-62 | NB298-63 | NB355-20 | NB355-53 | NB435-63 | NB435-03 | NB488-34 | NB488-37 |
|---|---|---|---|---|---|---|---|---|---|---|---|---|
| Cetearyl Alcohol | 1.20 | 1.20 | 1.20 | 1.20 | 1.20 | 1.80 | 1.50 | 1.20 | 2.25 | 2.25 | 2.25 | 3.00 |
| 2-Ethylhexyl Palmitate | 1.50 | 1.50 | 1.50 | 1.50 | 1.50 | 2.25 | 1.88 | 1.50 | 2.25 | 2.25 | 4.50 | 6.00 |
| Dicetyl Phosphate | 1.20 | 1.20 | 1.20 | 1.20 | 1.20 | 1.80 | 1.50 | 1.20 | 1.58 | 1.58 | 1.575 | 2.100 |
| Ceteareth-10 Phosphate | 0.60 | 0.60 | 0.60 | 0.60 | 0.60 | 0.90 | 0.75 | 0.60 | 0.68 | 0.68 | 0.675 | 0.900 |
| Theobroma Grandiflorum Seed Butter | 1.00 | 1.00 | 1.00 | 1.00 | 1.00 | 1.00 | 1.00 | 1.00 | 1.50 | 1.50 | | |
| Shea Butter | | | | | | | | | | | 1.50 | 2.00 |
| Steareth-10 | 0.90 | 0.90 | 0.90 | 0.90 | 0.90 | 0.90 | 0.80 | 0.90 | 1.35 | 1.35 | 1.35 | 1.35 |
| Tocopheryl Acetate | 0.50 | 0.50 | 0.50 | 0.50 | 0.50 | 0.50 | 0.50 | 0.50 | 0.50 | 0.50 | 0.50 | 0.50 |
| Dimethicone | 1.00 | 1.00 | 1.00 | 1.00 | 1.00 | 1.00 | 1.00 | 1.00 | 1.00 | 1.00 | 1.00 | 1.00 |
| Bisabolol | 1.20 | 1.20 | 1.20 | 1.20 | 1.20 | 1.20 | 1.20 | 1.20 | 0.20 | | 0.20 | 0.20 |
| BHT | 0.10 | 0.10 | 0.10 | 0.10 | 0.10 | 0.10 | 0.10 | 0.10 | 0.10 | 0.10 | 0.10 | 0.10 |

Figure 2

| Component (%) | NB298-54A | NB298-54B | NB298-54C | NB298-54E | NB298-82 | NB298-93 | NB355-20 | NB355-53 | NB435-83 | NB435-03 | NB488-34 | NB488-37 |
|---|---|---|---|---|---|---|---|---|---|---|---|---|
| Propylene Glycol | 2.50 | 2.50 | 2.50 | 2.50 | 2.50 | 2.50 | 2.50 | 2.50 | 2.50 | 2.50 | 2.50 | |
| Pentylene Glycol | | | | | | | | | | | | 2.50 |
| Glycerin | 5.00 | 5.00 | 5.00 | 5.00 | 5.00 | 5.00 | 5.00 | 5.00 | 5.00 | 5.00 | 5.00 | 5.00 |
| Methylparaben | 0.30 | 0.30 | 0.30 | 0.30 | 0.30 | 0.30 | 0.30 | | | | | |
| Propylparaben | 0.10 | 0.10 | 0.10 | 0.10 | 0.10 | 0.10 | 0.10 | | | | | |
| Disodium EDTA | 0.10 | 0.10 | 0.10 | 0.10 | 0.10 | 0.10 | 0.10 | 0.10 | 0.10 | 0.10 | 0.10 | 0.10 |
| DI Water | 77.36 | 77.35 | 77.35 | 77.35 | 78.35 | 78.10 | 77.21 | 78.75 | 77.19 | 77.49 | 78.50 | 72.725 |
| Sodium Phosphate Monobasic | | | | | | | | | | | 0.20 | |
| Sodium Phosphate Dibasic | | | | | | | | | | | | 0.283 |
| Citric Acid | | | | | | | | | | | | 0.192 |
| Sodium Hydroxide (10% Sol) | q.s. (pH 6) | q.s. (pH 6) | q.s. (pH 6) | q.s. (pH 6) | q.s. (pH 6) | q.s. (pH 6) | q.s. (pH 6) | q.s. (pH 6) | q.s. (pH 6) | q.s. (pH 6) | | |
| Urea | 1.25 | 1.25 | 1.25 | 1.25 | 1.25 | 1.25 | 1.25 | 1.25 | 1.25 | 1.25 | | |

Figure 3

| Component (%) | NB296-54A | NB296-54B | NB296-54C | NB296-54E | NB296-92 | NB296-93 | NB355-20 | NB35 5-53 | NB43 5-83 | NB43 5-03 | NB48 8-34 | NB48 8-37 |
|---|---|---|---|---|---|---|---|---|---|---|---|---|
| Sodium Hyaluronate | 0.10 | 0.10 | 0.10 | 0.10 | 0.10 | 0.10 | 0.10 | 0.10 | 0.10 | 0.10 | 0.10 | 0.10 |
| Aloe | 0.50 | 0.50 | 0.50 | 0.50 | 0.50 | 0.50 | 0.50 | 0.50 | 0.50 | 0.50 | | |
| Melaleuca alternifolia (Standard Tea Tree Oil) | 1.00 | 0.80 | 0.80 | 0.50 | | | | | | | | |
| Melaleuca ericifolia (Lavender Tea Tree Oil) | | 0.19 | 0.20 | 0.50 | | | | | | | | |
| Leptospermum petersonii (Lemon Tea Tree Oil) | | 0.01 | 0.01 | 0.01 | | | | | | | | |
| Piroctone Olamine | 1.00 | 1.00 | 1.00 | 1.00 | 1.00 | 1.00 | 1.00 | 1.00 | 1.00 | 1.00 | 1.00 | 1.00 |
| Glycyrrhetinic Acid | 0.75 | 0.75 | 0.75 | 0.75 | 0.75 | 0.75 | 0.75 | 0.75 | 0.10 | | | 0.10 |
| Allantoin | 0.75 | 0.75 | 0.75 | 0.75 | 0.75 | 0.75 | 0.75 | 0.75 | 0.75 | 0.75 | 0.75 | 0.75 |
| Vitis Vinifera (Grapeseed) Extract | 0.10 | 0.10 | 0.10 | 0.10 | 0.10 | 0.10 | 0.10 | 0.10 | 0.10 | 0.10 | 0.10 | 0.10 |

Figure 4

| Product | Form | Density |
|---|---|---|
| NB296-92 | Aerosol Foam | 0.22 g/cm$^3$ |
| NB296-93 | Aerosol Foam | 0.27 g/cm$^3$ |
| Promiseb™ | Cream | 0.91 g/cm$^3$ |

Figure 5

| TEST | RESULT | |
|---|---|---|
| | NB435-63 | NB488-37 |
| Primary Skin Irritation Test | No edema or erythema at 24, 48 or 72 hours. | No edema or erythema at 24, 48 or 72 hours. |
| Kligman Maximization Test - Direct Contact | Weak Sensitizer, no visible changes seen after challenge following sensitization induction. | Weak sensitizer, no visible changes seen after challenge following sensitization induction. |

Figure 6

| | Promiseb | NB435-63 |
|---|---|---|
| Time | Mean ± Std Dev | Mean ± Std Dev |
| Initial | 18.6 ± 1.8 | 18.4 ± 1.9 |
| 0.5 hours | 33.5 ± 4.8 | 31.9 ± 4.6 |
| 1.0 hours | 28.0 ± 3.5 | 47.9 ± 4.6 |
| 2.0 hours | 27.1 ± 2.7 | 48.7 ± 3.5 |
| 4.0 hours | 21.8 ± 2.6 | 50.4 ± 2.3 |
| 6.0 hours | 24.0 ± 2.6 | 52.7 ± 1.9 |

| Test Article | Subject Number | Reaction | Duration |
|---|---|---|---|
| Promiseb | 4 | Application site erythema and puritis | 30 min – 6 hours |
| | 5 | Application site erythema | 30 min – 6 hours |
| | 7 | Application site erythema and puritis | 30 min – 4 hours |

EMOLLIENT FOAMS FOR TREATMENT OF SEBORRHEIC DERMATITIS

RELATED APPLICATIONS

This application claims the benefit of priority to U.S. Provisional Patent Application Ser. No. 61/315,101, filed Mar. 18, 2010; the contents of which are hereby incorporated by reference.

BACKGROUND

Dermatoses are common diseases of the skin that take many forms, including seborrheic dermatitis. Dermatoses present with several symptoms, including desquamation, erythema, pruritus, inflammation, lichenification, and scaling. In general, dermatoses alter the stratum corneum structure, in turn compromising barrier function and leading to increased transepidermal water loss (TEWL) and exposure to environmental irritants. TEWL is indicative of a disturbed barrier function, and has been correlated to pruritus (itch) intensity in patients. Improvement in skin barrier function prevents the penetration of contact allergens and irritants into the epidermal layer, leading to reductions in inflammation, erythema, desquamation, and scaling. Improved skin moisturization reduces the appearance of scaling improving self image.

More specifically, seborrheic dermatitis is a common disease of the skin presenting with dry or greasy scaling of the scalp, hairline and nasolabial folds, sometimes accompanied by itching. In more severe cases, yellowish to reddish scaly pimples appear along the hairline, behind the ears, in the ear canal, on the eyebrows, on the bridge of the nose, around the nose, on the chest, and on the upper back.

Topical drug treatments for seborrheic dermatitis include steroids, antifungals, and keratolytics. In addition to drug treatments, seborrheic dermatitis can be managed through the use of drug-free medical devices.

SUMMARY OF THE INVENTION

In certain embodiments, the invention relates to an emulsion, comprising: an oil phase, wherein the oil phase comprises an emulsifier or surfactant, a first moisturizer or first emollient, a first antioxidant or first preservative, and a first fragrance; and an aqueous phase, wherein the aqueous phase comprises a vehicle, a second moisturizer or second emollient, a second antioxidant or second preservative, and a pH adjuster.

In certain embodiments, the invention relates to a composition, comprising: an oil phase, wherein the oil phase comprises an emulsifier or surfactant, a first moisturizer or first emollient, a first antioxidant or first preservative, and a first fragrance; an aqueous phase, wherein the aqueous phase comprises a vehicle, a second moisturizer or second emollient, a second antioxidant or second preservative, and a pH adjuster; a propellant; and a purge gas.

In certain embodiments, the invention relates to a method of treating a dermatosis, comprising the step of applying to an affected area of a subject in need thereof a therapeutically-effective amount of any one of the aforementioned emulsions or compositions. In certain embodiments, the invention relates to any one of the aforementioned methods, wherein the dermatosis is seborrheic dermatitis.

BRIEF DESCRIPTION OF THE FIGURES

FIG. 1 tabulates various components that may be present in the oil phase of emulsions or compositions of the invention.

FIG. 2 tabulates various components that may be present in the aqueous phase of emulsions or compositions of the invention.

FIG. 3 tabulates various components that may be present in the emulsions or compositions of the invention.

FIG. 4 depicts the densities of two compositions of the present invention in comparison to the density of a commercially-available cream.

FIG. 5 tabulates biocompatibility data of aerosol foam compositions of the invention.

FIG. 6 tabulates the change from initial moisture values following treatment with a composition of the invention and a comparative composition.

DETAILED DESCRIPTION OF THE INVENTION

Overview

Figures 7, 8:
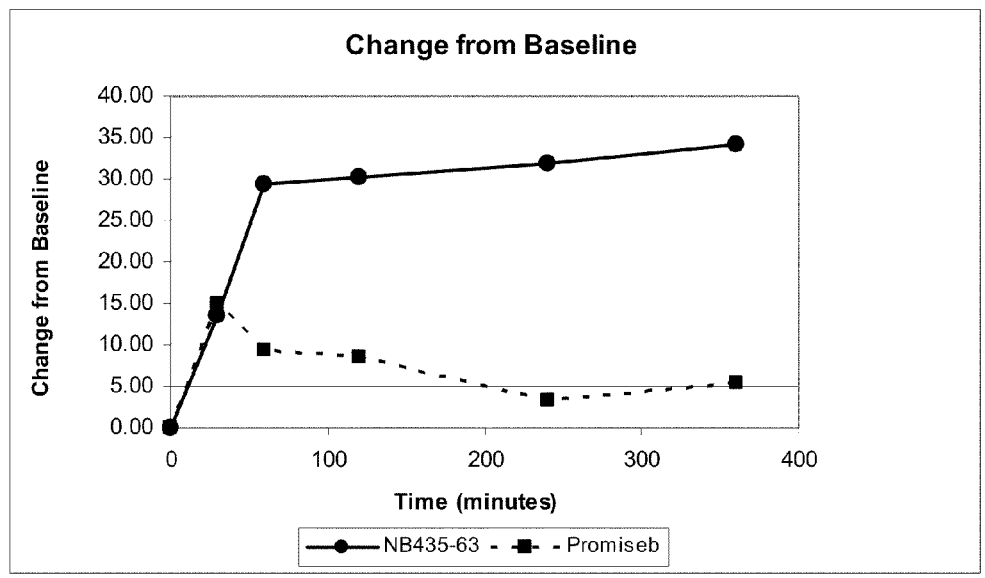
FIG. 7 graphically depicts the increase in stratum corneum moisture content following treatment with a composition of the invention and a comparative composition.
FIG. 8 tabulates the treatment emergent adverse events observed during skin tolerability testing.

In certain embodiments, the invention relates to oil-in-water emulsions. In certain embodiments, the compositions do not contain volatile lower alcohols (e.g., ethanol). In certain embodiments, the compositions comprise an aerosol propellant. In certain embodiments, the aerosol propellant is a hydrofluoroalkane propellant (HFA). In certain embodiments, the compositions produce a foam upon actuation of an aerosol container charged with the composition. In certain embodiments, the foams are stable against collapse. In certain embodiments, the foams are both time- and temperature-stable. In certain embodiments, the foams rub-in quickly without a greasy residue. In certain embodiments, the foam is moisturizing. In certain embodiments, the foam is non-irritating.

In certain embodiments, the dispensed foam is suitable for the management of seborrheic dermatitis, and exerts its therapeutic effect without the inclusion of an active pharmaceutical ingredient. In certain embodiments, these "drug-free" compositions are equally or more therapeutically-effective than prescription creams and lotions for the management of the signs and symptoms of seborrheic dermatitis. In certain embodiments, the dispensed foam has a density between about 0.05 and about 0.5 g/cm$^3$, is easily spread over large body surface areas, is time- and temperature-stable, moisturizes the skin, and/or is non-irritating. In certain embodiments, the foam rapidly collapses when subjected to shear forces, allowing for quick and efficient application to large body surface areas. In certain embodiments, skin moisture levels continue to be improved up to eight hours after application of a composition to the skin.

Propellants

There are several possible choices of propellants for an aerosol foam, including, but not limited to, CFCs, hydrocarbons, compressed gases, and HFAs. The Montreal Protocol has banned the use of CFCs (chlorofluorocarbons) due to their ability to deplete the ozone layer. Montreal Protocol on Substances that Deplete the Ozone Layer, United Nations Environmental Programme, 1987. In contrast, hydrocarbon propellants demonstrate very low reactivity and good resistance to free-radical attack. However, hydrocarbon propellants are highly flammable. Moreover, compressed inert gases, such as nitrogen and carbon dioxide, can be used as an aerosol propellant. While offering good chemical stability due to their inertness, they are unable to provide consistent product delivery throughout the life of an aerosol can due to their high vapor pressures. Fortunately, HFAs (hydrofluoroalkanes, also known as hydrofluorocarbons, or HFCs) are pharmaceutically acceptable, generally non-reactive, and ozone-friendly.

DEFINITIONS

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, a "cream" is an opaque, viscous, non-greasy to mildly-greasy emulsion or suspension semisolid intended for external application to the skin that tends to mostly evaporate or be absorbed when rubbed into the skin. The material contains <50% of hydrocarbons or polyethylene glycols as the vehicle and/or >20% volatiles (as measured by loss on drying to a constant weight at about 105° C.).

As used herein, a "lotion" is an opaque, thin, non-greasy emulsion-based liquid intended for external application to the skin that tends to evaporate rapidly with a cooling sensation when rubbed into the skin. The material generally contains a water based composition with >50% volatiles (as measured by loss on drying to a constant weight at about 105° C.).

Exemplary Constituents of Emulsions and Compositions of the Invention

Exemplary identities of various constituents of the emulsions and compositions of the present invention are described below.

1. Propellants

In one embodiment, the propellant is a HFA or a mixture of one or more hydrofluoroalkanes. Suitable hydrofluoroalkanes include 1,1,1,2-tetrafluoroethane (HFA 134a); 1,1,1,2,3,3,3-heptafluoropropane (HFA 227); and mixtures and admixtures of these and other HFAs that are currently approved or may become approved for medical use are suitable. Hydrocarbon as well as chlorofluorocarbon (CFC) propellants can also be used in the present invention.

2. Vehicles

Suitable topical vehicles and vehicle components for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as propylene glycol, pentylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol and dimethicone copolyol; hydrocarbon-based materials such as petrolatum and squalane; and other vehicles and vehicle components that are suitable for administration to the skin, as well as mixtures of topical vehicle components as identified above or otherwise known to the art.

In one embodiment, the compositions of the present invention are oil-in-water emulsions. Liquids suitable for use in formulating compositions of the present invention include water, and water-miscible solvents such as glycols (e.g., ethylene glycol, butylene glycol, isoprene glycol, propylene glycol, pentylene glycol), glycerol, liquid polyols, dimethyl sulfoxide, and isopropyl alcohol. One or more aqueous vehicles may be present.

In one embodiment, formulations without methanol, ethanol, propanols, or butanols are desirable.

3. Surfactants and Emulsifiers

Many topical formulations contain chemical emulsions which use surface active ingredients (emulsifiers) to disperse dissimilar chemicals in a particular solvent system. For example, most lipid-like (oily or fatty) or lipophilic ingredients do not uniformly disperse in aqueous solvents unless they are first combined with emulsifiers, which form microscopic aqueous soluble structures that contain a lipophilic interior and a hydrophilic exterior, resulting in an oil-in-water emulsion. In order to be soluble in aqueous media, a molecule must be polar or charged so as to favorably interact with water molecules, which are also polar. Similarly, to dissolve an aqueous-soluble polar or charged ingredient in a largely lipid or oil-based solvent, an emulsifier is typically used which forms stable structures that contain the hydrophilic components in the interior of the structure while the exterior is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion droplet. Emulsion destabilization results in the aqueous and lipophilic ingredients separating into two layers, potentially destroying the commercial value of a topical product.

Surfactants suitable for use in the present invention may be ionic or non-ionic. These include, but are not limited to: polysorbates (e.g., Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), Polysorbate 80 (polyoxyethylene (20) sorbitan monooleate)), steareth-10 (or other octadecyl polyoxyethylene ethers), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide diethanolamine (lauramide DEA), cocamide DEA, cocamide monoethanolamine (coamide MEA), oleyl betaine, cocamidopropyl betaine, cocamidopropyl phosphatidyl PG-dimonium chloride, dicetyl phosphate (dihexadecyl phosphate), ceteareth-10 phosphate, and methylbenzethonium chloride. Appropriate combinations or mixtures of such surfactants may also be used according to the present invention.

Many of these surfactants may also serve as emulsifiers in formulations of the present invention.

Other suitable emulsifiers for use in the formulations of the present invention include, but are not limited to, behentrimonium methosulfate-cetearyl alcohol, non-ionic emulsifiers like emulsifying wax, polyoxyethylene oleyl ether, polyethylene glycol-40 stearate (PEG-40 stearate), cetostearyl alcohol (cetearyl alcohol), ceteareth-12, ceteareth-20, ceteareth-30, ceteareth alcohol, glyceryl stearate, PEG-100 stearate, glyceryl stearate and PEG-100 stearate, steareth-2 and steareth-20, or combinations/mixtures thereof, as well as cationic emulsifiers like stearamidopropyl dimethylamine and behentrimonium methosulfate, or combinations/mixtures thereof 4. Moisturizers, Emollients, and Humectants One of the most important aspects of topical products in general, and cosmetic products in particular, is the consumer's perception of the aesthetic qualities of a product. For example, white petrolatum is an excellent moisturizer and skin product, it is rarely used alone, especially on the face, because it is greasy, sticky, does not rub easily into the skin and may soil clothing. Consumers highly value products which are aesthetically elegant and have an acceptable tactile feel and performance on their skin.

Suitable moisturizers for use in the formulations of the present invention include, but are not limited to, lactic acid and other hydroxy acids and their salts, glycerol, propylene glycol, pentylene glycol, butylene glycol, sodium salt of pyrrolidone carbonic acid (sodium PCA), sodium hyaluronate, or polyethylene glycol (PEG) (e.g., CARBOWAX PEG 200, CARBOWAX PEG 400, or CARBOWAX PEG 800).

Suitable emollients or humectants for use in the formulations of the present invention include, but are not limited to, cetyl palmitate, glycerol (glycerin), polypropylene glycol-15 stearyl ether (PPG-15 stearyl ether), lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, pentylene glycol, *Theobroma grandiflorum* seed butter, shea butter, ceramides (e.g., ceramide 2 or ceramide 3), hydroxypropyl bispalmitamide MEA, hydroxypropyl bislauramide MEA, hydroxypropyl bisisostearamide MEA, 1,3-bis-(N-2-(hydroxyethyl)stearoylamino)-2-hydroxy propane, bis-hydroxyethyl tocopherylsuccinoylamido hydroxypropane, urea, aloe, allantoin, glycyrrhetinic acid, and dicaprylate/dicaprate.

In addition, appropriate combinations and mixtures of any of these moisturizing agents and emollients may be used in accordance with the present invention.

5. Preservatives and Antioxidants

The composition may further include components adapted to improve the stability or effectiveness of the applied formulation.

Suitable preservatives for use in the present invention include, but are not limited to: ureas, such as imidazolidinyl urea and diazolidinyl urea; phenoxyethanol; sodium methyl paraben, methylparaben, ethylparaben, and propylparaben; potassium sorbate; sodium benzoate; sorbic acid; benzoic acid; formaldehyde; citric acid; sodium citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfite, butylated hydroxytoluene, butylated hydroxyanisole, tocopherols (such as α-tocopherol), tocopheryl acetate, sodium ascorbate/ascorbic acid, ascorbyl palmitate, propyl gallate, and chelating agents like ethylenediaminetetraacetic acid (EDTA) (e.g., disodium EDTA), citric acid, and sodium citrate.

In certain embodiments, antioxidants or preservatives of the present invention may also function as a moisturizer or emollient, for example.

In addition, combinations or mixtures of these preservatives or anti-oxidants may also be used in the formulations of the present invention.

6. Viscosity Modifiers

Suitable viscosity adjusting agents (i.e., thickening and thinning agents) for use in the formulations of the present invention include, but are not limited to, protective colloids or non-ionic gums such as hydroxyethylcellulose, xanthan gum, and sclerotium gum, as well as magnesium aluminum silicate, silica, microcrystalline wax, beeswax, paraffin, and cetyl palmitate. In addition, appropriate combinations or mixtures of these viscosity adjusters may be utilized according to the present invention.

7. Additional Constituents

Additional constituents suitable for incorporation into the emulsions of the present invention include, but are not limited to: skin protectants, adsorbents, demulcents, emollients, moisturizers, buffering agents, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, and pH adjusters (e.g., citric acid, sodium hydroxide, sodium phosphate monobasic, and sodium phosphate dibasic).

For example, lipids normally found in healthy skin (or their functional equivalents) may be incorporated into the emulsions of the present invention. In certain embodiments, the lipid is selected from the group consisting of ceramides, cholesterol, and free fatty acids. In certain embodiments, the lipid is a ceramide. In certain embodiments, the lipid is selected from the group consisting of ceramide 1, ceramide 2, ceramide 3, ceramide 4, ceramide 5, and ceramide 6. In certain embodiments, the lipid is selected from the group consisting of hydroxypropyl bispalmitamide MEA, hydroxypropyl bislauramide MEA, hydroxypropyl bisisostearamide MEA, 1,3-bis-(N-2-(hydroxyethyl) stearoylamino)-2-hydroxy propane, and bis-hydroxyethyl tocopherylsuccinoylamido hydroxypropane.

Examples of skin soothing agents include, but are not limited to, allantoin, aloe, avocado oil, green tea extract, hops extract, chamomile extract, colloidal oatmeal, calamine, cucumber extract, and combinations thereof.

Examples of vitamins include, but are not limited to, vitamins A, D, E, K, and combinations thereof.

Examples of sunscreens include, but are not limited to, p-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, disodium phenyl dibenzimidazole tetrasulfonate, diethylamino hydroxybenzoyl hexyl benzoate, octyl triazone, diethylhexyl butamido triazone, polysilicone-15, and combinations thereof.

Suitable fragrances and colors may be used in the formulations of the present invention. Examples of fragrances and colors suitable for use in topical products are known in the art. Examples of fragrances include, but are not limited to, bisabolol, *Melaleuca alternifolia* oil, *Melaleuca ericafolia* oil, and *Leptospermum petersonni* oil.

Often, one constituent of a composition may accomplish several functions. In one embodiment, the present invention relates to constituents that may act as a lubricant, an emollient, or a skin-penetrating agent. In one embodiment, the multi-functional constituent is socetyl stearate, isopropyl isostearate, isopropyl palmitate, or isopropyl myristate.

8. Purging Gases

In one embodiment, the air in the container charged with the composition is replaced by an inert gas. In certain embodiments, the inert gas is selected from the group consisting of argon, nitrogen, and mixtures thereof.

Exemplary Emulsions of the Invention

In certain embodiments, the invention relates to an emulsion, comprising:
  an oil phase, wherein the oil phase comprises an emulsifier or surfactant, a first moisturizer or first emollient, a first antioxidant or first preservative, and a fragrance; and
  an aqueous phase, wherein the aqueous phase comprises water, a second moisturizer or second emollient, a second antioxidant or second preservative, and a pH adjuster.

In certain embodiments, the invention relates to an emulsion, consisting essentially of:
  an oil phase, wherein the oil phase consists essentially of an emulsifier or surfactant, a first moisturizer or first emollient, a first antioxidant or first preservative, and a fragrance; and
  an aqueous phase, wherein the aqueous phase consists essentially of water, a second moisturizer or second emollient, a second antioxidant or second preservative, and a pH adjuster.

In certain embodiments, the invention relates to an emulsion, consisting of:
  an oil phase, wherein the oil phase consists of an emulsifier or surfactant, a first moisturizer or first emollient, a first antioxidant or first preservative, and a fragrance; and
  an aqueous phase, wherein the aqueous phase consists of water, a second moisturizer or second emollient, a second antioxidant or second preservative, and a pH adjuster.

In certain embodiments, the invention relates to an emulsion, comprising:
  cetearyl alcohol, from about 0.5% to about 5% by weight of the emulsion;
  dicetyl phosphate, from about 0.5% to about 3% by weight of the emulsion;
  ceteareth-10 phosphate, from about 0.3% to about 1.5% by weight of the emulsion;
  steareth-10, from about 0.4% to about 2.0% by weight of the emulsion;
  2-ethylhexyl palmitate, from about 0.7% to about 9.0% by weight of the emulsion;
  shea butter, from about 0.5% to about 3.0% by weight of the emulsion;
  dimethicone, from about 0.5% to about 1.5% by weight of the emulsion;
  glycyrrhetinic acid, from about 0.3% to about 1.5% by weight of the emulsion;
  tocopheryl acetate, from about 0.2% to about 0.8% by weight of the emulsion;
  butylated hydroxytoluene, from about 0.05% to about 0.2% by weight of the emulsion;
  bisabolol, from about 0.05% to about 2% by weight of the emulsion;

water, from about 60% to about 90% by weight of the emulsion;
pentylene glycol, from about 1.2% to about 3.8% by weight of the emulsion;
glycerol, from about 2% to about 8% by weight of the emulsion;
sodium hyaluronate, from about 0.05% to about 0.2% by weight of the emulsion;
allantoin, from about 0.3% to about 1.2% by weight of the emulsion;
disodium EDTA, from about 0.05% to about 0.2% by weight of the emulsion;
piroctone olamine, from about 0.5% to about 1.5% by weight of the emulsion;
*Vitis vinifera* extract, from about 0.05% to about 0.2% by weight of the emulsion;
sodium phosphate dibasic, from about 0.14% to about 0.32% by weight of the emulsion; and
citric acid, from about 0.1% to about 0.3% by weight of the emulsion.

In certain embodiments, the invention relates to an emulsion, consisting essentially of:
cetearyl alcohol, from about 0.5% to about 5% by weight of the emulsion;
dicetyl phosphate, from about 0.5% to about 3% by weight of the emulsion;
ceteareth-10 phosphate, from about 0.3% to about 1.5% by weight of the emulsion;
steareth-10, from about 0.4% to about 2.0% by weight of the emulsion;
2-ethylhexyl palmitate, from about 0.7% to about 9.0% by weight of the emulsion;
shea butter, from about 0.5% to about 3.0% by weight of the emulsion;
dimethicone, from about 0.5% to about 1.5% by weight of the emulsion;
glycyrrhetinic acid, from about 0.3% to about 1.5% by weight of the emulsion;
tocopheryl acetate, from about 0.2% to about 0.8% by weight of the emulsion;
butylated hydroxytoluene, from about 0.05% to about 0.2% by weight of the emulsion;
bisabolol, from about 0.05% to about 2% by weight of the emulsion;
water, from about 60% to about 90% by weight of the emulsion;
pentylene glycol, from about 1.2% to about 3.8% by weight of the emulsion;
glycerol, from about 2% to about 8% by weight of the emulsion;
sodium hyaluronate, from about 0.05% to about 0.2% by weight of the emulsion;
allantoin, from about 0.3% to about 1.2% by weight of the emulsion;
disodium EDTA, from about 0.05% to about 0.2% by weight of the emulsion;
piroctone olamine, from about 0.5% to about 1.5% by weight of the emulsion;
*Vitis vinifera* extract, from about 0.05% to about 0.2% by weight of the emulsion;
sodium phosphate dibasic, from about 0.14% to about 0.32% by weight of the emulsion; and
citric acid, from about 0.1% to about 0.3% by weight of the emulsion.

In certain embodiments, the invention relates to an emulsion, consisting of:
cetearyl alcohol, from about 0.5% to about 5% by weight of the emulsion;
dicetyl phosphate, from about 0.5% to about 3% by weight of the emulsion;
ceteareth-10 phosphate, from about 0.3% to about 1.5% by weight of the emulsion;
steareth-10, from about 0.4% to about 2.0% by weight of the emulsion;
2-ethylhexyl palmitate, from about 0.7% to about 9.0% by weight of the emulsion;
shea butter, from about 0.5% to about 3.0% by weight of the emulsion;
dimethicone, from about 0.5% to about 1.5% by weight of the emulsion;
glycyrrhetinic acid, from about 0.3% to about 1.5% by weight of the emulsion;
tocopheryl acetate, from about 0.2% to about 0.8% by weight of the emulsion;
butylated hydroxytoluene, from about 0.05% to about 0.2% by weight of the emulsion;
bisabolol, from about 0.05% to about 2% by weight of the emulsion;
water, from about 60% to about 90% by weight of the emulsion;
pentylene glycol, from about 1.2% to about 3.8% by weight of the emulsion;
glycerol, from about 2% to about 8% by weight of the emulsion;
sodium hyaluronate, from about 0.05% to about 0.2% by weight of the emulsion;
allantoin, from about 0.3% to about 1.2% by weight of the emulsion;
disodium EDTA, from about 0.05% to about 0.2% by weight of the emulsion;
piroctone olamine, from about 0.5% to about 1.5% by weight of the emulsion;
*Vitis vinifera* extract, from about 0.05% to about 0.2% by weight of the emulsion;
sodium phosphate dibasic, from about 0.14% to about 0.32% by weight of the emulsion; and
citric acid, from about 0.1% to about 0.3% by weight of the emulsion.

In certain embodiments, the invention relates to an emulsion, comprising:
cetearyl alcohol, from about 0.5% to about 2% by weight of the emulsion;
dicetyl phosphate, from about 0.5% to about 2% by weight of the emulsion;
ceteareth-10 phosphate, from about 0.3% to about 1% by weight of the emulsion;
steareth-10, from about 0.4% to about 1.3% by weight of the emulsion;
2-ethylhexyl palmitate, from about 0.7% to about 2.3% by weight of the emulsion;
*Theobroma grandiflorum* seed butter, from about 0.5% to about 1.5% by weight of the emulsion;
dimethicone, from about 0.5% to about 1.5% by weight of the emulsion;
glycyrrhetinic acid, from about 0.3% to about 1.2% by weight of the emulsion;
tocopheryl acetate, from about 0.2% to about 0.8% by weight of the emulsion;
butylated hydroxytoluene, from about 0.05% to about 0.2% by weight of the emulsion;
bisabolol, from about 0.5% to about 2% by weight of the emulsion;

water, from about 60% to about 90% by weight of the emulsion;
propylene glycol, from about 1.2% to about 3.8% by weight of the emulsion;
glycerol, from about 2% to about 8% by weight of the emulsion;
urea, from about 0.5% to about 2% by weight of the emulsion;
sodium hyaluronate, from about 0.05% to about 0.2% by weight of the emulsion;
aloe, from about 0.2% to about 0.8% by weight of the emulsion;
allantoin, from about 0.3% to about 1.2% by weight of the emulsion;
disodium EDTA, from about 0.05% to about 0.2% by weight of the emulsion;
piroctone olamine, from about 0.5% to about 1.5% by weight of the emulsion;
*Vitis vinifera* extract, from about 0.05% to about 0.2% by weight of the emulsion; and
sodium hydroxide.

In certain embodiments, the invention relates to an emulsion, consisting essentially of:
cetearyl alcohol, from about 0.5% to about 2% by weight of the emulsion;
dicetyl phosphate, from about 0.5% to about 2% by weight of the emulsion;
ceteareth-10 phosphate, from about 0.3% to about 1% by weight of the emulsion;
steareth-10, from about 0.4% to about 1.3% by weight of the emulsion;
2-ethylhexyl palmitate, from about 0.7% to about 2.3% by weight of the emulsion;
*Theobroma grandiflorum* seed butter, from about 0.5% to about 1.5% by weight of the emulsion;
dimethicone, from about 0.5% to about 1.5% by weight of the emulsion;
glycyrrhetinic acid, from about 0.3% to about 1.2% by weight of the emulsion;
tocopheryl acetate, from about 0.2% to about 0.8% by weight of the emulsion;
butylated hydroxytoluene, from about 0.05% to about 0.2% by weight of the emulsion;
bisabolol, from about 0.5% to about 2% by weight of the emulsion;
water, from about 60% to about 90% by weight of the emulsion;
propylene glycol, from about 1.2% to about 3.8% by weight of the emulsion;
glycerol, from about 2% to about 8% by weight of the emulsion;
urea, from about 0.5% to about 2% by weight of the emulsion;
sodium hyaluronate, from about 0.05% to about 0.2% by weight of the emulsion;
aloe, from about 0.2% to about 0.8% by weight of the emulsion;
allantoin, from about 0.3% to about 1.2% by weight of the emulsion;
disodium EDTA, from about 0.05% to about 0.2% by weight of the emulsion;
piroctone olamine, from about 0.5% to about 1.5% by weight of the emulsion;
*Vitis vinifera* extract, from about 0.05% to about 0.2% by weight of the emulsion; and
sodium hydroxide.

In certain embodiments, the invention relates to an emulsion, consisting of:
cetearyl alcohol, from about 0.5% to about 2% by weight of the emulsion;
dicetyl phosphate, from about 0.5% to about 2% by weight of the emulsion;
ceteareth-10 phosphate, from about 0.3% to about 1% by weight of the emulsion;
steareth-10, from about 0.4% to about 1.3% by weight of the emulsion;
2-ethylhexyl palmitate, from about 0.7% to about 2.3% by weight of the emulsion;
*Theobroma grandiflorum* seed butter, from about 0.5% to about 1.5% by weight of the emulsion;
dimethicone, from about 0.5% to about 1.5% by weight of the emulsion;
glycyrrhetinic acid, from about 0.3% to about 1.2% by weight of the emulsion;
tocopheryl acetate, from about 0.2% to about 0.8% by weight of the emulsion;
butylated hydroxytoluene, from about 0.05% to about 0.2% by weight of the emulsion;
bisabolol, from about 0.5% to about 2% by weight of the emulsion;
water, from about 60% to about 90% by weight of the emulsion;
propylene glycol, from about 1.2% to about 3.8% by weight of the emulsion;
glycerol, from about 2% to about 8% by weight of the emulsion;
urea, from about 0.5% to about 2% by weight of the emulsion;
sodium hyaluronate, from about 0.05% to about 0.2% by weight of the emulsion;
aloe, from about 0.2% to about 0.8% by weight of the emulsion;
allantoin, from about 0.3% to about 1.2% by weight of the emulsion;
disodium EDTA, from about 0.05% to about 0.2% by weight of the emulsion;
piroctone olamine, from about 0.5% to about 1.5% by weight of the emulsion;
*Vitis vinifera* extract, from about 0.05% to about 0.2% by weight of the emulsion; and
sodium hydroxide.

In certain embodiments, the invention relates to an emulsion, comprising:
cetearyl alcohol, in about 3.0% by weight of the emulsion;
dicetyl phosphate, in about 2.1% by weight of the emulsion;
ceteareth-10 phosphate, in about 0.9% by weight of the emulsion;
steareth-10, in about 1.4% by weight of the emulsion;
2-ethylhexyl palmitate, in about 6.0% by weight of the emulsion;
shea butter, in about 2.0% by weight of the emulsion;
dimethicone, in about 1.0% by weight of the emulsion;
glycyrrhetinic acid, in about 0.1% by weight of the emulsion;
tocopheryl acetate, in about 0.5% by weight of the emulsion;
butylated hydroxytoluene, in about 0.1% by weight of the emulsion;
bisabolol, in about 0.2% by weight of the emulsion;
water, in about 72.7% by weight of the emulsion;
pentylene glycol, in about 2.5% by weight of the emulsion;
glycerol, in about 5.0% by weight of the emulsion;

sodium hyaluronate, in about 0.1% by weight of the emulsion;
allantoin, in about 0.8% by weight of the emulsion;
disodium EDTA, in about 0.1% by weight of the emulsion;
piroctone olamine, in about 1.0% by weight of the emulsion;
Vitis vinifera extract, in about 0.1% by weight of the emulsion;
sodium phosphate dibasic, in about 0.3% by weight of the emulsion; and
citric acid, in about 0.2% by weight of the emulsion.

In certain embodiments, the invention relates to an emulsion, consisting essentially of:
cetearyl alcohol, in about 3.0% by weight of the emulsion;
dicetyl phosphate, in about 2.1% by weight of the emulsion;
ceteareth-10 phosphate, in about 0.9% by weight of the emulsion;
steareth-10, in about 1.4% by weight of the emulsion;
2-ethylhexyl palmitate, in about 6.0% by weight of the emulsion;
shea butter, in about 2.0% by weight of the emulsion;
dimethicone, in about 1.0% by weight of the emulsion;
glycyrrhetinic acid, in about 0.1% by weight of the emulsion;
tocopheryl acetate, in about 0.5% by weight of the emulsion;
butylated hydroxytoluene, in about 0.1% by weight of the emulsion;
bisabolol, in about 0.2% by weight of the emulsion;
water, in about 72.7% by weight of the emulsion;
pentylene glycol, in about 2.5% by weight of the emulsion;
glycerol, in about 5.0% by weight of the emulsion;
sodium hyaluronate, in about 0.1% by weight of the emulsion;
allantoin, in about 0.8% by weight of the emulsion;
disodium EDTA, in about 0.1% by weight of the emulsion;
piroctone olamine, in about 1.0% by weight of the emulsion;
Vitis vinifera extract, in about 0.1% by weight of the emulsion;
sodium phosphate dibasic, in about 0.3% by weight of the emulsion; and
citric acid, in about 0.2% by weight of the emulsion.

In certain embodiments, the invention relates to an emulsion, consisting of:
cetearyl alcohol, in about 3.0% by weight of the emulsion;
dicetyl phosphate, in about 2.1% by weight of the emulsion;
ceteareth-10 phosphate, in about 0.9% by weight of the emulsion;
steareth-10, in about 1.4% by weight of the emulsion;
2-ethylhexyl palmitate, in about 6.0% by weight of the emulsion;
shea butter, in about 2.0% by weight of the emulsion;
dimethicone, in about 1.0% by weight of the emulsion;
glycyrrhetinic acid, in about 0.1% by weight of the emulsion;
tocopheryl acetate, in about 0.5% by weight of the emulsion;
butylated hydroxytoluene, in about 0.1% by weight of the emulsion;
bisabolol, in about 0.2% by weight of the emulsion;
water, in about 72.7% by weight of the emulsion;
pentylene glycol, in about 2.5% by weight of the emulsion;
glycerol, in about 5.0% by weight of the emulsion;
sodium hyaluronate, in about 0.1% by weight of the emulsion;
allantoin, in about 0.8% by weight of the emulsion;
disodium EDTA, in about 0.1% by weight of the emulsion;
piroctone olamine, in about 1.0% by weight of the emulsion;
Vitis vinifera extract, in about 0.1% by weight of the emulsion;
sodium phosphate dibasic, in about 0.3% by weight of the emulsion; and
citric acid, in about 0.2% by weight of the emulsion.

In certain embodiments, the invention relates to an emulsion, comprising:
cetearyl alcohol, in about 1.2% by weight of the emulsion;
dicetyl phosphate, in about 1.2% by weight of the emulsion;
ceteareth-10 phosphate, in about 0.6% by weight of the emulsion;
steareth-10, in about 0.9% by weight of the emulsion;
2-ethylhexyl palmitate, in about 1.5% by weight of the emulsion;
Theobroma grandiflorum seed butter, in about 1.0% by weight of the emulsion;
dimethicone, in about 1.0% by weight of the emulsion;
glycyrrhetinic acid, in about 0.8% by weight of the emulsion;
tocopheryl acetate, in about 0.5% by weight of the emulsion;
butylated hydroxytoluene, in about 0.1% by weight of the emulsion;
bisabolol, in about 1.2% by weight of the emulsion;
water, in about 78.8% by weight of the emulsion;
propylene glycol, in about 2.5% by weight of the emulsion;
glycerol, in about 5.0% by weight of the emulsion;
urea, in about 1.2% by weight of the emulsion;
sodium hyaluronate, in about 0.1% by weight of the emulsion;
aloe, in about 0.5% by weight of the emulsion;
allantoin, in about 0.8% by weight of the emulsion;
disodium EDTA, in about 0.1% by weight of the emulsion;
piroctone olamine, in about 1.0% by weight of the emulsion;
Vitis vinifera extract, in about 0.1% by weight of the emulsion; and
sodium hydroxide.

In certain embodiments, the invention relates to an emulsion, consisting essentially of:
cetearyl alcohol, in about 1.2% by weight of the emulsion;
dicetyl phosphate, in about 1.2% by weight of the emulsion;
ceteareth-10 phosphate, in about 0.6% by weight of the emulsion;
steareth-10, in about 0.9% by weight of the emulsion;
2-ethylhexyl palmitate, in about 1.5% by weight of the emulsion;
Theobroma grandiflorum seed butter, in about 1.0% by weight of the emulsion;
dimethicone, in about 1.0% by weight of the emulsion;
glycyrrhetinic acid, in about 0.8% by weight of the emulsion;
tocopheryl acetate, in about 0.5% by weight of the emulsion;
butylated hydroxytoluene, in about 0.1% by weight of the emulsion;
bisabolol, in about 1.2% by weight of the emulsion;
water, in about 78.8% by weight of the emulsion;
propylene glycol, in about 2.5% by weight of the emulsion;

glycerol, in about 5.0% by weight of the emulsion;
urea, in about 1.2% by weight of the emulsion;
sodium hyaluronate, in about 0.1% by weight of the emulsion;
aloe, in about 0.5% by weight of the emulsion;
allantoin, in about 0.8% by weight of the emulsion;
disodium EDTA, in about 0.1% by weight of the emulsion;
piroctone olamine, in about 1.0% by weight of the emulsion;
*Vitis vinifera* extract, in about 0.1% by weight of the emulsion; and
sodium hydroxide.

In certain embodiments, the invention relates to an emulsion, consisting of:
cetearyl alcohol, in about 1.2% by weight of the emulsion;
dicetyl phosphate, in about 1.2% by weight of the emulsion;
ceteareth-10 phosphate, in about 0.6% by weight of the emulsion;
steareth-10, in about 0.9% by weight of the emulsion;
2-ethylhexyl palmitate, in about 1.5% by weight of the emulsion;
*Theobroma grandiflorum* seed butter, in about 1.0% by weight of the emulsion;
dimethicone, in about 1.0% by weight of the emulsion;
glycyrrhetinic acid, in about 0.8% by weight of the emulsion;
tocopheryl acetate, in about 0.5% by weight of the emulsion;
butylated hydroxytoluene, in about 0.1% by weight of the emulsion;
bisabolol, in about 1.2% by weight of the emulsion;
water, in about 78.8% by weight of the emulsion;
propylene glycol, in about 2.5% by weight of the emulsion;
glycerol, in about 5.0% by weight of the emulsion;
urea, in about 1.2% by weight of the emulsion;
sodium hyaluronate, in about 0.1% by weight of the emulsion;
aloe, in about 0.5% by weight of the emulsion;
allantoin, in about 0.8% by weight of the emulsion;
disodium EDTA, in about 0.1% by weight of the emulsion;
piroctone olamine, in about 1.0% by weight of the emulsion;
*Vitis vinifera* extract, in about 0.1% by weight of the emulsion; and
sodium hydroxide.

In certain embodiments, the invention relates to any one of the aforementioned emulsions provided that it does not comprise methylparaben, propyl paraben, $C_{12}$-$C_{15}$ alkyl benzoates, ceramide 2, ceramide 3, hydroxypropyl bispalmitamide MEA, petrolatum, *Melaleuca alternifolia* oil, *Melaleuca ericifolia* oil, or *Leptospermum petersonni* oil.

Exemplary Components of the Oil Phase

In certain embodiments, the invention relates to any one of the aforementioned emulsions, wherein the emulsifier or surfactant is selected from the group consisting of: polysorbate 20, polysorbate 40, polysorbate 60, polysorbate 80, steareth-10, sodium dodecyl sulfate, lauryl dimethyl amine oxide, cetyltrimethylammonium bromide, polyethoxylated alcohols, polyoxyethylene sorbitan, octoxynol, N,N-dimethyldodecylamine-N-oxide, hexadecyltrimethylammonium bromide, polyoxyl 10 lauryl ether, sodium deoxycholate, sodium cholate, polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate, ceteareth-10 phosphate, methylbenzethonium chloride, behentrimonium methosulfate-cetearyl alcohol, emulsifying wax, polyoxyethylene oleyl ether, PEG-40 stearate, cetostearyl alcohol, ceteareth-12, ceteareth-20, ceteareth-30, ceteareth alcohol, glyceryl stearate, PEG-100 stearate, glyceryl stearate, PEG-100 stearate, steareth-2, steareth-20, stearamidopropyl dimethylamine, and behentrimonium methosulfate, and combinations/mixtures thereof.

In certain embodiments, the invention relates to any one of the aforementioned emulsions, wherein the emulsifier or surfactant is selected from the group consisting of cetearyl alcohol, dicetyl phosphate, ceteareth-10 phosphate, and steareth-10, and combinations/mixtures thereof.

In certain embodiments, the invention relates to any one of the aforementioned emulsions, wherein the emulsifier or surfactant is present in an amount from about 1.5% to about 11% by weight of the emulsion. In certain embodiments, the emulsifier or surfactant is present in an amount from about 2% to about 10% by weight of the emulsion. In certain embodiments, the emulsifier or surfactant is present in an amount of about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% by weight of the emulsion.

In certain embodiments, the invention relates to any one of the aforementioned emulsions, wherein the emulsifier or surfactant comprises cetostearyl alcohol (cetearyl alcohol). In certain embodiments, the cetostearyl alcohol is present in an amount from about 0.5% to about 5% by weight of the emulsion. In certain embodiments, the cetostearyl alcohol is present in an amount from about 0.6% to about 4% by weight of the emulsion. In certain embodiments, cetostearyl alcohol is present in about 0.6%, about 0.8%, about 1.0%, about 1.2%, about 1.4%, about 1.6%, about 2.05, about 2.5%, about 3.0%, about 3.5%, or about 4.0% by weight of the emulsion.

In certain embodiments, the invention relates to any one of the aforementioned emulsions, wherein the emulsifier or surfactant comprises dicetyl phosphate. In certain embodiments, the dicetyl phosphate is present in an amount from about 0.5% to about 4% by weight of the emulsion. In certain embodiments, the dicetyl phosphate is present in an amount from about 0.6% to about 3% by weight of the emulsion. In certain embodiments, dicetyl phosphate is present in about 0.6%, about 0.8%, about 1.0%, about 1.2%, about 1.4%, about 1.6%, about 1.8%, about 2.0%, about 2.2%, about 2.4%, about 2.6%, about 2.8%, or about 3.0% by weight of the emulsion.

In certain embodiments, the invention relates to any one of the aforementioned emulsions, wherein the emulsifier or surfactant comprises ceteareth-10 phosphate. In certain embodiments, the ceteareth-10 phosphate is present in an amount from about 0.3% to about 2.0% by weight of the emulsion. In certain embodiments, the ceteareth-10 phosphate is present in an amount from about 0.4% to about 1.5% by weight of the emulsion. In certain embodiments, ceteareth-10 phosphate is present in about 0.4%, about 0.5%, about 0.6%, about 0.7%, about 0.8%, about 0.9%, about 1.0%, about 1.1%, about 1.2%, about 1.3%, about 1.4%, or about 1.5% by weight of the emulsion.

In certain embodiments, the invention relates to any one of the aforementioned emulsions, wherein the emulsifier or surfactant comprises steareth-10. In certain embodiments, the steareth-10 is present in an amount from about 0.4% to about 2.5% by weight of the emulsion. In certain embodiments, the steareth-10 is present in an amount from about 0.6% to about 2.0% by weight of the emulsion. In certain embodiments, steareth-10 is present in about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0% by weight of the emulsion.

In certain embodiments, the invention relates to any one of the aforementioned emulsions, wherein the first moisturizer or first emollient is selected from the group consisting of petrolatum, lactic acid, glycerol, propylene glycol, pentylene glycol, butylene glycol, sodium PCA, sodium hyaluronate, polyethylene glycol (e.g., CARBOWAX PEG 200, CARBOWAX PEG 400, or CARBOWAX PEG 800), cetyl palmitate, glycerol, PPG-15 stearyl ether, lanolin alcohol, lanolin, lanolin derivatives, cholesterol, isostearyl neopentanoate, octyl stearate, mineral oil, isocetyl stearate, myristyl myristate, octyl dodecanol, 2-ethylhexyl palmitate, dimethicone, phenyl trimethicone, cyclomethicone, $C_{12}$-$C_{15}$ alkyl benzoates, dimethiconol, *Theobroma grandiflorum* seed butter, shea butter, ceramide 2, ceramide 3, hydroxypropyl bispalmitamide MEA, urea, aloe, allantoin, glycyrrhetinic acid, hydroxypropyl bislauramide MEA, hydroxypropyl bisisostearamide MEA, 1,3-bis-(N-2-(hydroxyethyl)stearoylamino)-2-hydroxy propane, bis-hydroxyethyl tocopherylsuccinoylamido hydroxypropane, and dicaprylate/dicaprate, and combinations/mixtures thereof.

In certain embodiments, the invention relates to any one of the aforementioned emulsions, wherein the first moisturizer or first emollient is selected from the group consisting of 2-ethylhexyl palmitate, *Theobroma grandiflorum* seed butter, shea butter, dimethicone, glycyrrhetinic acid, and combinations/mixtures thereof.

In certain embodiments, the invention relates to any one of the aforementioned emulsions, wherein the first moisturizer or first emollient is present in an amount from about 2% to about 14% by weight of the emulsion. In certain embodiments, the first moisturizer or first emollient is present in an amount from about 3% to about 12% by weight of the emulsion. In certain embodiments, the first moisturizer or first emollient is present in an amount of about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, or about 12% by weight of the emulsion.

In certain embodiments, the invention relates to any one of the aforementioned emulsions, wherein the first moisturizer or first emollient comprises 2-ethylhexyl palmitate. In certain embodiments, the 2-ethylhexyl palmitate is present in an amount from about 0.7% to about 9% by weight of the emulsion. In certain embodiments, the 2-ethylhexyl palmitate is present in an amount from about 1.0% to about 8% by weight of the emulsion. In certain embodiments, the 2-ethylhexyl palmitate is present in about 1.0%, about 1.1%, about 1.2%, about 1.3%, about 1.4%, about 1.5%, about 1.6%, about 1.7%, about 1.8%, about 1.9%, about 2.0%, a bout 2.5%, about 3%, about 3.5%, about 4%, about 4.5%, about 5%, about 5.5%, about 6%, about 6.5%, about 7%, about 7.5%, or about 8% by weight of the emulsion.

In certain embodiments, the invention relates to any one of the aforementioned emulsions, wherein the first moisturizer or first emollient comprises *Theobroma grandiflorum* seed butter. In certain embodiments, the *Theobroma grandiflorum* seed butter is present in an amount from about 0.5% to about 1.5% by weight of the emulsion. In certain embodiments, the *Theobroma grandiflorum* seed butter is present in an amount from about 0.7% to about 1.3% by weight of the emulsion. In certain embodiments, *Theobroma grandiflorum* seed butter is present in about 0.7%, about 0.8%, about 0.9%, about 1.0%, about 1.1%, about 1.2%, or about 1.3% by weight of the emulsion.

In certain embodiments, the invention relates to any one of the aforementioned emulsions, wherein the first moisturizer or first emollient comprises shea butter. In certain embodiments, the shea butter is present in an amount from about 1.0% to about 3.0% by weight of the emulsion. In certain embodiments, the shea butter is present in an amount from about 1.5% to about 2.5% by weight of the emulsion. In certain embodiments, shea butter is present in about 1.5%, about 1.6%, about 1.7%, about 1.8%, about 1.9%, about 2.0%, about 2.1%, about 2.2%, about 2.3%, about 2.4%, or about 2.5% by weight of the emulsion.

In certain embodiments, the invention relates to any one of the aforementioned emulsions, wherein the first moisturizer or first emollient comprises dimethicone. In certain embodiments, the dimethicone is present in an amount from about 0.5% to about 1.5% by weight of the emulsion. In certain embodiments, the dimethicone is present in an amount from about 0.7% to about 1.3% by weight of the emulsion. In certain embodiments, dimethicone is present in about 0.7%, about 0.8%, about 0.9%, about 1.0%, about 1.1%, about 1.2%, or about 1.3% by weight of the emulsion.

In certain embodiments, the invention relates to any one of the aforementioned emulsions, wherein the first moisturizer or first emollient comprises glycyrrhetinic acid. In certain embodiments, glycyrrhetinic acid is present in an amount from about 0.05% to about 1.2% by weight of the emulsion. In certain embodiments, the glycyrrhetinic acid is present in an amount from about 0.05% to about 1.1% by weight of the emulsion. In certain embodiments, the glycyrrhetinic acid is present in about 0.05%, about 0.1%, about 0.15%, about 0.2%, about 0.25%, about 0.3%, about 0.4%, about 0.5%, about 0.6%, about 0.7%, about 0.8%, about 0.9%, about 1.0% or about 1.1% by weight of the emulsion.

In certain embodiments, the invention relates to any one of the aforementioned emulsions, wherein the first antioxidant or first preservative is selected from the group consisting of imidazolidinyl urea, diazolidinyl urea, phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, benzalkonium chloride, benzethonium chloride, cetrimide, dequalinium chloride, cetylpyridinium chloride, phenylmercuric nitrate, phenylmercuric acetate, thimerosal, piroctone olamine, *Vitis vinifera* seed oil, chlorobutanol, dichlorobenzyl alcohol, phenylethyl alcohol, benzyl alcohol, ascorbic acid, sodium bisulfite, butylated hydroxytoluene, butylated hydroxyanisole, α-tocopherol, tocopheryl acetate, sodium ascorbate/ascorbic acid, ascorbyl palmitate, propyl gallate, disodium EDTA, citric acid, and sodium citrate, and combinations/mixtures thereof.

In certain embodiments, the invention relates to any one of the aforementioned emulsions, wherein the first antioxidant or first preservative is selected from the group consisting of tocopheryl acetate, butylated hydroxytoluene, and combinations/mixtures thereof.

In certain embodiments, the invention relates to any one of the aforementioned emulsions, wherein the first antioxidant or first preservative is present in an amount from about 0.3% to about 0.9% by weight of the emulsion. In certain embodiments, the first antioxidant or first preservative is present in an amount from about 0.4% to about 0.8% by weight of the emulsion. In certain embodiments, the first antioxidant or first preservative is present in an amount of about 0.4%, about 0.5%, about 0.6%, about 0.7%, or about 0.8% by weight of the emulsion.

In certain embodiments, the invention relates to any one of the aforementioned emulsions, wherein the first antioxidant or first preservative comprises tocopheryl acetate. In certain embodiments, the tocopheryl acetate is present in an amount from about 0.2% to about 0.8% by weight of the emulsion. In certain embodiments, the tocopheryl acetate is present in an amount from about 0.3% to about 0.7% by weight of the emulsion. In certain embodiments, tocopheryl acetate is present in about 0.3%, about 0.4%, about 0.5%, about 0.6%, or about 0.7% by weight of the emulsion.

In certain embodiments, the invention relates to any one of the aforementioned emulsions, wherein the first antioxidant or first preservative comprises butylated hydroxytoluene. In certain embodiments, the butylated hydroxytoluene is present in an amount from about 0.05% to about 0.2% by weight of the emulsion. In certain embodiments, the butylated hydroxytoluene is present in an amount from about 0.05% to about 0.15% by weight of the emulsion. In certain embodiments, butylated hydroxytoluene is present in about 0.05%, about 0.06%, about 0.07%, about 0.08%, about 0.09%, about 0.1%, about 0.11%, about 0.12%, about 0.13%, about 0.14%, or about 0.15% by weight of the emulsion.

In certain embodiments, the invention relates to any one of the aforementioned emulsions, wherein the fragrance is selected from the group consisting of bisabolol, *Melaleuca alternifolia* oil, *Melaleuca ericafolia* oil, and *Leptospermum petersonni* oil, and combinations/mixtures thereof.

In certain embodiments, the invention relates to any one of the aforementioned emulsions, wherein the fragrance consists of bisabolol.

In certain embodiments, the invention relates to any one of the aforementioned emulsions, wherein the fragrance is present in an amount from about 0.05% to about 3.0% by weight of the emulsion. In certain embodiments, the fragrance is present in an amount from about 0.1% to about 1.6% by weight of the emulsion. In certain embodiments, the fragrance is present in an amount of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, or about 1.6% by weight of the emulsion.

In certain embodiments, the invention relates to any one of the aforementioned emulsions, wherein the fragrance comprises bisabolol. In certain embodiments, the bisabolol is present in an amount from about 0.05% to about 2.0% by weight of the emulsion. In certain embodiments, bisabolol is present in an amount from about 0.1% to about 1.6% by weight of the emulsion. In certain embodiments, the bisabolol is present in an amount of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, or about 1.6% by weight of the emulsion.

Exemplary Components of the Aqueous Phase

Each of the aforementioned emulsions comprises an aqueous phase. The components described below may be present in the aqueous phase of any one of the aforementioned emulsions.

In certain embodiments, the invention relates to any one of the aforementioned emulsions, wherein water is present in an amount about 60% to about 90% by weight of the emulsion. In certain embodiments, water is present in an amount from about 65% to about 85% by weight of the emulsion. In certain embodiments, water is present in an amount of about 66%, about 68%, about 70%, about 72%, about 74%, about 76%, about 78%, about 80%, about 82%, or about 84% by weight of the emulsion.

In certain embodiments, the invention relates to any one of the aforementioned emulsions, wherein the second moisturizer or second emollient is selected from the group consisting of petrolatum, lactic acid, glycerol, propylene glycol, pentylene glycol, butylene glycol, sodium PCA, sodium hyaluronate, polyethylene glycol (e.g., CARBOWAX PEG 200, CARBOWAX PEG 400, or CARBOWAX PEG 800), cetyl palmitate, glycerol, PPG-15 stearyl ether, lanolin alcohol, lanolin, lanolin derivatives, cholesterol, isostearyl neopentanoate, octyl stearate, mineral oil, isocetyl stearate, myristyl myristate, octyl dodecanol, 2-ethylhexyl palmitate, dimethicone, phenyl trimethicone, cyclomethicone, $C_{12}$-$C_{15}$ alkyl benzoates, dimethiconol, *Theobroma grandiflorum* seed butter, shea butter, ceramide 2, ceramide 3, hydroxypropyl bispalmitamide MEA, hydroxypropyl bislauramide MEA, hydroxypropyl bisisostearamide MEA, 1,3-bis-(N-2-(hydroxyethyl)stearoylamino)-2-hydroxy propane, bis-hydroxyethyl tocopherylsuccinoylamido hydroxypropane, urea, aloe, allantoin, glycyrrhetinic acid, and dicaprylate/dicaprate, and combinations/mixtures thereof.

In certain embodiments, the invention relates to any one of the aforementioned emulsions, wherein the second moisturizer or second emollient is selected from the group consisting of propylene glycol, pentylene glycol, glycerol, urea, sodium hyaluronate, aloe, allantoin, and combinations/mixtures thereof.

In certain embodiments, the invention relates to any one of the aforementioned emulsions, wherein the second moisturizer or second emollient is present in an amount from about 5% to about 17% by weight of the emulsion. In certain embodiments, the second moisturizer or second emollient is present in an amount from about 7% to about 15% by weight of the emulsion. In certain embodiments, the second moisturizer or second emollient is present in an amount of about 7%, about 8%, about 9%, about 10%, about 11%, about 12%, about 13%, about 14%, or about 15% by weight of the emulsion.

In certain embodiments, the invention relates to any one of the aforementioned emulsions, wherein the second moisturizer or second emollient comprises propylene glycol. In certain embodiments, the propylene glycol is present in an amount from about 1.2% to about 3.8% by weight of the emulsion. In certain embodiments, the propylene glycol is present in an amount from about 1.5% to about 3.5% by weight of the emulsion. In certain embodiments, the propylene glycol is present in about 1.5%, about 2%, about 2.5%, about 3%, or about 3.5% by weight of the emulsion.

In certain embodiments, the invention relates to any one of the aforementioned emulsions, wherein the second moisturizer or second emollient comprises pentylene glycol. In certain embodiments, the pentylene glycol is present in an amount from about 1.2% to about 3.8% by weight of the emulsion. In certain embodiments, the pentylene glycol is present in an amount from about 1.5% to about 3.5% by weight of the emulsion. In certain embodiments, the pentylene glycol is present in about 1.5%, about 2%, about 2.5%, about 3%, or about 3.5% by weight of the emulsion.

In certain embodiments, the invention relates to any one of the aforementioned emulsions, wherein the second moisturizer or second emollient comprises glycerol. In certain embodiments, the glycerol is present in an amount from about 2% to about 8% by weight of the emulsion. In certain embodiments, the glycerol is present in an amount from about 3% to about 7% by weight of the emulsion. In certain embodiments, the glycerol is present in about 3%, about 3.5%, about 4%, about 4.5%, about 5%, about 5.5%, about 6%, about 6.5%, or about 7% by weight of the emulsion.

In certain embodiments, the invention relates to any one of the aforementioned emulsions, wherein the second moisturizer or second emollient comprises urea. In certain embodiments, the urea is present in an amount from about 0.5% to about 2% by weight of the emulsion. In certain embodiments, the urea is present in an amount from about 0.8% to about 1.6% by weight of the emulsion. In certain embodiments, the urea is present in about 0.8%, about 1.0%, about 1.2%, about 1.4%, or about 1.6% by weight of the emulsion.

In certain embodiments, the invention relates to any one of the aforementioned emulsions, wherein the second moisturizer or second emollient comprises sodium hyaluronate. In certain embodiments, the sodium hyaluronate is present in an amount from about 0.05% to about 0.2% by weight of the emulsion. In certain embodiments, the sodium hyaluronate is present in an amount from about 0.1% to about 0.12% by weight of the emulsion. In certain embodiments, the sodium hyaluronate is present in about 0.1%, about 0.09%, about 0.1%, about 0.11%, or about 0.12% by weight of the emulsion.

In certain embodiments, the invention relates to any one of the aforementioned emulsions, wherein the second moisturizer or second emollient comprises aloe. In certain embodiments, the aloe is present in an amount from about 0.2% to about 0.8% by weight of the emulsion. In certain embodiments, the aloe is present in an amount from about 0.3% to about 0.7% by weight of the emulsion. In certain embodiments, the aloe is present in about 0.3%, about 0.4%, about 0.5%, about 0.6%, or about 0.7% by weight of the emulsion.

In certain embodiments, the invention relates to any one of the aforementioned emulsions, wherein the second moisturizer or second emollient comprises allantoin. In certain embodiments, the allantoin is present in an amount from about 0.3% to about 1.2% by weight of the emulsion. In certain embodiments, the allantoin is present in an amount from about 0.4% to about 1.1% by weight of the emulsion. In certain embodiments, the allantoin is present in about 0.4%, about 0.5%, about 0.6%, about 0.7%, about 0.8%, about 0.9%, about 1.0%, or about 1.1% by weight of the emulsion.

In certain embodiments, the invention relates to any one of the aforementioned emulsions, wherein the second antioxidant or second preservative is selected from the group consisting of imidazolidinyl urea, diazolidinyl urea, phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, benzalkonium chloride, benzethonium chloride, cetrimide, dequalinium chloride, cetylpyridinium chloride, phenylmercuric nitrate, phenylmercuric acetate, thimerosal, piroctone olamine, *Vitis vinifera* seed oil, chlorobutanol, dichlorobenzyl alcohol, phenylethyl alcohol, benzyl alcohol, ascorbic acid, sodium bisulfite, butylated hydroxytoluene, butylated hydroxyanisole, α-tocopherol, tocopheryl acetate, sodium ascorbate/ascorbic acid, ascorbyl palmitate, propyl gallate, disodium EDTA, citric acid, and sodium citrate, and combinations/mixtures thereof.

In certain embodiments, the invention relates to any one of the aforementioned emulsions, wherein the second antioxidant or second preservative is selected from the group consisting of disodium EDTA, piroctone olamine, and *Vitis vinifera* extract, and combinations/mixtures thereof.

In certain embodiments, the invention relates to any one of the aforementioned emulsions, wherein the second antioxidant or second preservative is present in an amount from about 0.6% to about 1.8% by weight of the emulsion. In certain embodiments, the second antioxidant or second preservative is present in an amount from about 0.8% to about 1.6% by weight of the emulsion. In certain embodiments, the second antioxidant or second preservative is present in an amount of about 0.8%, about 1.0%, about 1.2%, about 1.4%, or about 1.6% by weight of the emulsion.

In certain embodiments, the invention relates to any one of the aforementioned emulsions, wherein the second antioxidant or second preservative comprises disodium EDTA. In certain embodiments, the disodium EDTA is present in an amount from about 0.05% to about 0.2% by weight of the emulsion. In certain embodiments, the disodium EDTA is present in an amount from about 0.08% to about 0.12% by weight of the emulsion. In certain embodiments, the disodium EDTA is present in about 0.08%, about 0.09%, about 0.1%, about 0.11%, or about 0.12% by weight of the emulsion.

In certain embodiments, the invention relates to any one of the aforementioned emulsions, wherein the second antioxidant or second preservative comprises piroctone olamine. In certain embodiments, the piroctone olamine is present in an amount from about 0.5% to about 1.5% by weight of the emulsion. In certain embodiments, the piroctone olamine is present in an amount from about 0.8% to about 1.2% by weight of the emulsion. In certain embodiments, the piroctone olamine is present in about 0.8%, about 0.9%, about 1.0%, about 1.1%, or about 1.2% by weight of the emulsion.

In certain embodiments, the invention relates to any one of the aforementioned emulsions, wherein the second antioxidant or second preservative comprises *Vitis vinifera* extract. In certain embodiments, the *Vitis vinifera* extract is present in an amount from about 0.05% to about 0.2% by weight of the emulsion. In certain embodiments, the *Vitis vinifera* extract is present in an amount from about 0.08% to about 0.12% by weight of the emulsion. In certain embodiments, the *Vitis vinifera* extract is present in about 0.08%, about 0.09%, about 0.1%, about 0.11%, or about 0.12% by weight of the emulsion.

In certain embodiments, the invention relates to any one of the aforementioned emulsions, wherein the pH adjuster is selected from the group consisting of citric acid, sodium hydroxide, and sodium phosphate monobasic, sodium phosphate dibasic, and combinations/mixtures thereof.

In certain embodiments, the invention relates to any one of the aforementioned emulsions, wherein the pH adjuster comprises sodium phosphate dibasic and citric acid.

In certain embodiments, the invention relates to any one of the aforementioned emulsions, wherein the pH of the emulsion is from about 4.0 to about 7.5. In certain embodiments, the pH of the emulsion is from about 4.5 to about 6.5. In certain embodiments, the pH of the emulsion is about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0.

Exemplary Compositions of the Invention

In certain embodiments, the invention relates to a composition comprising:
  any one of the aforementioned emulsions;
  a propellant; and
  a purge gas.

In certain embodiments, the invention relates to a composition consisting essentially of:
  any one of the aforementioned emulsions;
  a propellant; and
  a purge gas.

In certain embodiments, the invention relates to a composition consisting of:
  any one of the aforementioned emulsions;

a propellant; and a purge gas.

Exemplary Propellants

Each of the aforementioned compositions comprises a propellant. The propellants described below may be present in any one of the aforementioned compositions.

In certain embodiments, the invention relates to any one of the aforementioned compositions, wherein the propellant is selected from the group consisting of 1,1,1,2-tetrafluoroethane, 1,1,1,2,3,3,3-heptafluoropropane, and combinations/mixtures thereof.

In certain embodiments, the invention relates to any one of the aforementioned compositions, wherein the propellant is present in an amount from about 3% to about 20% by weight of the composition. In certain embodiments, the invention relates to any one of the aforementioned compositions, wherein the propellant is present in an amount from about 5% to about 18% by weight of the composition. In certain embodiments, the invention relates to any one of the aforementioned compositions, wherein the propellant is about 5%, about 6%, about 7%, about 8%, about 9%, about 10%, about 11%, about 12%, about 13%, about 14%, about 15%, about 16%, about 17%, or about 18% by weight of the composition.

Exemplary Purge Gases

Each of the aforementioned compositions comprises a purge gas. The purge gases described below may be present in any one of the aforementioned compositions.

In certain embodiments, the invention relates to any one of the aforementioned compositions, wherein the purge gas is selected from the group consisting of nitrogen and argon. In certain embodiments, the purge gas is argon.

In certain embodiments, the invention relates to any one of the aforementioned compositions, wherein the purge gas is present in an amount from about 0.4% to about 6% by weight of the composition. In certain embodiments, the purge gas is present in an amount from about 0.8% to about 5% by weight of the composition. In certain embodiments, the purge gas is about 0.8%, about 1%, about 1.2%, about 1.4%, about 1.6%, about 1.8%, about 2%, about 2.2%, about 2.5%, about 2.6%, about 2.8%, about 3%, about 3.2%, about 3.4%, about 3.6%, about 3.8%, about 4%, about 4.2%, about 4.4%, about 4.6%, about 4.8% or about 5% by weight of the composition.

Exemplary Properties of Emulsions and Compositions of the Invention

In certain embodiments, the invention relates to any one of the aforementioned emulsions or compositions that, upon application to the skin of an affected subject, is non-irritating.

In certain embodiments, the invention relates to any one of the aforementioned emulsions or compositions that, upon application to the skin of an affected subject, is well-tolerated.

In certain embodiments, the invention relates to any one of the aforementioned emulsions or compositions that, upon application to the skin of an affected subject, is weakly sensitizing. In certain embodiments, the invention relates to any one of the aforementioned emulsions or compositions that, upon application to the skin of an affected subject, is non-sensitizing.

In certain embodiments, the invention relates to any one of the aforementioned emulsions or compositions that, upon application to the skin of an affected subject, does not produce edema or erythema.

In certain embodiments, the invention relates to any one of the aforementioned emulsions or compositions that, upon application to the skin of an affected subject, moisturizes the skin.

In certain embodiments, the invention relates to any one of the aforementioned emulsions or compositions that, upon application to the skin of an affected subject, increases hydration of the skin.

In certain embodiments, the invention relates to any one of the aforementioned emulsions or compositions that, upon application to the skin of an affected subject, reduces transepidermal water loss.

In certain embodiments, the invention relates to any one of the aforementioned compositions that, upon expulsion from an aerosol container, forms a foam. In certain embodiments, the foam is temperature-stable. In certain embodiments, the foam is time-stable. In certain embodiments, the density of the foam is from about 0.05 to about 0.5 $g/cm^3$. In certain embodiments, the density of the foam is about 0.22 $g/cm^3$. In certain embodiments, the density of the foam is about 0.27 $g/cm^3$.

Exemplary Emulsions and Compositions of the Invention for Particular Uses

In certain embodiments, the invention relates to any one of the aforementioned emulsions or compositions for use in the treatment of a dermatosis.

In certain embodiments, the invention relates to any one of the aforementioned emulsions or compositions for use in the treatment of seborrheic dermatitis.

In certain embodiments, the invention relates to any one of the aforementioned emulsions or compositions for use in the treatment of a dermatosis, wherein the dermatosis is associated with desquamation, erythema, pruritus, inflammation, lichenification, excoriation, stinging, or scaling.

In certain embodiments, the invention relates to any one of the aforementioned emulsions or compositions for use in the treatment of a dermatosis of the scalp, including the hairline, ear canals, or behind the ears; the face, including the eyebrows, nose, or nasolabial folds; or the trunk, including the chest or back.

In certain embodiments, the invention relates to any one of the aforementioned emulsions or compositions for use in the treatment of a dermatosis, wherein the emulsion or composition is formulated for topical application once daily or twice daily.

Exemplary Methods of Use

In certain embodiments, the invention relates to a method of treating a dermatosis, comprising the step of applying to an affected area of a subject in need thereof a therapeutically-effective amount of any one of the aforementioned emulsions or compositions.

In certain embodiments, the invention relates to any one of the aforementioned methods, wherein the dermatosis is seborrheic dermatitis.

In certain embodiments, the invention relates to any one of the aforementioned methods, wherein the subject presents with desquamation, erythema, pruritus, inflammation, lichenification, excoriation, stinging, or scaling.

In certain embodiments, the invention relates to any one of the aforementioned methods, wherein the affected area is the scalp, including the hairline, ear canals, or behind the ears; the face, including the eyebrows, nose, or nasolabial folds; and the trunk, including the chest or back.

In certain embodiments, the invention relates to any one of the aforementioned methods, wherein the emulsion or composition is applied once daily or twice daily.

EXEMPLIFICATION

Example 1

Compositions and Method of Manufacture

An example product concentrate (NB296-54A; see FIGS. 1, 2, and 3) was manufactured using the procedure outlined below:

Part A: Oil Phase Preparation
1. Charge cetearyl alcohol, ethylhexyl palmitate, dicetyl phosphate, ceteareth-10 phosphate, *Theobroma grandiflorum* seed butter, steareth-10, dimethicone and butylated hydroxytoluene (BHT) into a Stainless Steel tank and heat to about 75-about 80° C.

Part B: Aqueous Phase Preparation
1. Charge Deionized Water, Propylene Glycol and Glycerin (glycerol) into a second Stainless Steel tank and heat to about 75-about 80° C.
2. Charge and dissolve Methylparaben, Propylparaben, Disodium EDTA and Urea while mixing.
3. Continue mixing until a clear solution is obtained while maintaining a temperature of about 75-about 80° C.

Part C: Final Emulsion Formation
1. Add Part A to Part B while high-shear mixing at about 75-about 80° C.
2. Cool the emulsion with an outside cold-water jacket to about 45-about 50° C. while high-shear mixing.
3. Discontinue high-shear mixing. Start low-shear mixing and continue cooling with cold-water jacket to form the vehicle emulsion.
4. When the temperature of the vehicle emulsion is about 37° C., add bisabolol, tocopheryl acetate, sodium hyaluronate, aloe, *Melaleuca alternifolia* oil, piroctone olamine, allantoin, *Vitis vinifera* seed oil and glycyrrhetinic acid; continue mixing until uniform.
5. Cool to about 27-about 32° C. Adjust to final pH with Sodium Hydroxide and final volume with DI water. Mix until uniform.

Following manufacturing of the Product Concentrate, the finished Product Concentrate was filled into aerosol cans as outlined below.
1. Aerosol cans are cleaned with compressed air and vacuum.
2. Product Concentrate is filled into cans.
3. Valves are placed onto the cans.
4. Cans are crimped and hydrofluorocarbon propellant is charged.
5. The aerosol can valve and dip-tube is purged with argon gas.

Propellant concentrations range from about 8-about 15% by weight of packaged product, argon concentrations range from about 0.8-about 4.0% by weight of packaged product.

Example 2

Product Densities

When dispensed from an aerosol can, the compositions of the invention form a foam. The densities of dispensed foam and non-foam medical devices intended to treat dermatoses were measured as follows.

Product was dispensed into a conical receptacle of known weight and volume. The product was dispensed into the receptacle so that there were no voids. Excess material was removed from the top of the receptacle with a flat-bladed spatula. The mass of the test article and receptacle was determined with the test article density calculated using the formula (Equation 1):

$$\text{Density} = (\text{MASS}_T - \text{MASS}_R)/\text{VOLUME}_R \quad (1)$$

Where:
$\text{MASS}_T$ = total mass of test article and receptacle
$\text{MASS}_R$ = mass of receptacle
$\text{VOLUME}_R$ = volume of receptacle Densities of various compositions of the invention are outlined in FIG. 4. In FIG. 4, Promiseb™ contains water, isohexadecane, butyrospermum parkii, pentylene glycol, ethylhexyl palmitate, cera alba, PEG-30 dipolyhydroxystearate, bisabolol, polyglyceryl-6 polyricinoleate, tocopheryl acetate, hydrogenated castor oil, acifructol complex, butylene glycol, magnesium sulfate, piroctone olamine, allantoin, magnesium stearate, disodium EDTA, Vitis vinifera, ascorbyl tetraisopalmitate, glycyrrhetinic acid, propyl gallate, and telmesteine (Promius Pharma).

Example 3

Product Biocompatibility

To demonstrate the inherent biocompatibility of the compositions of the invention and their suitability for use on diseased skin, biocompatibility testing was performed with selected compositions. Test selection was made in accordance with ISO 10993 guidelines for biocompatibility testing of surface medical devices in contact with skin.

The potential of the compositions of the invention to produce primary skin irritation in New Zealand White Rabbits was determined by examining the irritation produced by a single 4 hour topical skin exposure to a composition. The allergenic potential or sensitizing capacity of the compositions of the invention were examined by the Kligman Maximization—Direct Contact test in Hartley guinea pigs. See FIG. 5.

Example 4

Skin Moisturization

The measurement of the moisture content of the outermost layer of the skin (stratum corneum) by corneometry is a well established technique widely used in the development of cosmetic, pharmaceutical and medical device products. Corneometry is based on capacitance measurement of a dielectric medium. Any change in the dielectric constant due to variation in skin surface hydration alters the capacitance of a precision measuring capacitor. One of the greatest advantages of the capacitance measurement method, compared to other measurement methods, is the fact that products applied to the skin only have minimal influence on the measurements. Due to the sensitivity of the method, the measurement can detect small changes in hydration level. The materials used in the study were as follows:

MoistureMeter SC (Delfin Technologies, Ltd.) Serial Number: SC4M277
Pre-moistened Towelettes
Indelible Marker/Marking Template
NB435-63 Foam
Promiseb Topical Cream Two test articles were compared in the study—the commercially available Promiseb Topical Cream which is a drug-free medical device indicated for the treatment of seborrheic dermatitis; and NB-Foam. During the test session, both products were tested against each other. Products were applied using a paired comparison design between the left and right arms. As hair may interfere with the moisture measurements, test sites with the least amount of hair were selected.

1. Cleaned volar surfaces of both left and right arm with pre-moistened towelette and blotted dry.
2. Marked 4.0×4.0-cm test areas using an indelible marker on volar surface of left and right arms.
3. Measured the moisture content of all sites five (5) times using the MoistureMeter SC.
4. To minimize interference with the probe, selected the most hairless area within the test site. Began measurement by gently pressing the probe against the skin until three (3) green lights are showing. Measurement commenced when the unit beeped and stopped measuring after the second set of beeps. Recorded the measured skin moisture values.
5. Applied 400 mg of the each test article to the appropriate test area and completely rubbed-in.
6. At 30 minutes post application repeated steps 3 through 4.
7. At 1 hour post application repeated steps 3 through 4.
8. At 2 hours post application repeated steps 3 through 4.
9. At 4 hours post application repeated steps 3 through 4.
10. At 6 hours post application repeated steps 3 through 4.

Results are depicted in FIG. 6 and FIG. 7.

Example 5

Skin Tolerability

A ten subject study examining the tolerability of an inventive foam and Promiseb Topical Cream was conducted. The experimental procedure was as follows:

1. Cleaned volar surfaces of both left and right arm with pre-moistened towelette and blotted dry.
2. Marked 4.0×4.0-cm test areas using an indelible marker on volar surface of left and right arms.
3. Applied 400 mg of the each test article to the appropriate test area and completely rubbed-in.
4. At 30 minutes post application, observed application area for signs of irritation.
5. At 1 hour post application, observed application area for signs of irritation.
6. At 2 hours post application, observed application area for signs of irritation.
7. At 4 hours post application, observed application area for signs of irritation.
8. At 6 hours post application, observed application area for signs of irritation.

All observed reactions were minor and fully resolved following removal of test articles. Results are tabulated in FIG. 8.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating a dermatosis, comprising the step of applying to an affected area of a subject in need thereof a therapeutically-effective amount of a composition, wherein the composition comprises:
   an emulsion, wherein the emulsion comprises:
      cetearyl alcohol, from about 0.5% to about 5% by weight of the emulsion;
      dicetyl phosphate, from about 0.5% to about 3% by weight of the emulsion;
      ceteareth-10 phosphate, from about 0.3% to about 1.5% by weight of the emulsion;
      steareth-10, from about 0.4% to about 2.0% by weight of the emulsion;
      2-ethylhexyl palmitate, from about 0.7% to about 9.0% by weight of the emulsion;
      shea butter, from about 0.5% to about 3.0% by weight of the emulsion;
      dimethicone, from about 0.5% to about 1.5% by weight of the emulsion;
      glycyrrhetinic acid, from about 0.3% to about 1.5% by weight of the emulsion;
      tocopheryl acetate, from about 0.2% to about 0.8% by weight of the emulsion;
      butylated hydroxytoluene, from about 0.05% to about 0.2% by weight of the emulsion;
      bisabolol, from about 0.05% to about 2% by weight of the emulsion;
      water, from about 60% to about 90% by weight of the emulsion;
      pentylene glycol, from about 1.2% to about 3.8% by weight of the emulsion;
      glycerol, from about 2% to about 8% by weight of the emulsion;
      sodium hyaluronate, from about 0.05% to about 0.2% by weight of the emulsion;
      allantoin, from about 0.3% to about 1.2% by weight of the emulsion;
      disodium EDTA, from about 0.05% to about 0.2% by weight of the emulsion;
      piroctone olamine, from about 0.5% to about 1.5% by weight of the emulsion;
      *Vitis vinifera* extract, from about 0.05% to about 0.2% by weight of the emulsion;
      sodium phosphate dibasic, from about 0.14% to about 0.32% by weight of the emulsion; and
      citric acid, from about 0.1% to about 0.3% by weight of the emulsion;
   a propellant; and
   a purge gas.

2. The method of claim 1, wherein the dermatosis is seborrheic dermatitis.

3. The method of claim 1, wherein the subject presents with desquamation, erythema, pruritus, inflammation, lichenification, excoriation, stinging, or scaling.

4. The method of claim 1, wherein the affected area is the scalp, including the hairline, ear canals, or behind the ears; the face, including the eyebrows, nose, or nasolabial folds; and the trunk, including the chest or back.

5. The method of claim 1, wherein the composition is applied once daily or twice daily.

6. The method of claim 1, wherein the composition comprises
   an emulsion, wherein the emulsion comprises:
      cetearyl alcohol, in about 3.0% by weight of the emulsion;
      dicetyl phosphate, in about 2.1% by weight of the emulsion;

ceteareth-10 phosphate, in about 0.9% by weight of the emulsion;
steareth-10, in about 1.4% by weight of the emulsion;
2-ethylhexyl palmitate, in about 6.0% by weight of the emulsion;
shea butter, in about 2.0% by weight of the emulsion;
dimethicone, in about 1.0% by weight of the emulsion;
glycyrrhetinic acid, in about 0.1% by weight of the emulsion;
tocopheryl acetate, in about 0.5% by weight of the emulsion;
butylated hydroxytoluene, in about 0.1% by weight of the emulsion;
bisabolol, in about 0.2% by weight of the emulsion;
water, in about 72.7% by weight of the emulsion;
pentylene glycol, in about 2.5% by weight of the emulsion;
glycerol, in about 5.0% by weight of the emulsion;
sodium hyaluronate, in about 0.1% by weight of the emulsion;
allantoin, in about 0.8% by weight of the emulsion;
disodium EDTA, in about 0.1% by weight of the emulsion;
piroctone olamine, in about 1.0% by weight of the emulsion;
*Vitis vinifera* extract, in about 0.1% by weight of the emulsion;
sodium phosphate dibasic, in about 0.3% by weight of the emulsion; and
citric acid, in about 0.2% by weight of the emulsion;
a propellant; and
a purge gas.

7. The method of claim 1, wherein the propellant is selected from the group consisting of 1,1,1,2-tetrafluoroethane, 1,1,1,2,3,3,3-heptafluoropropane, and combinations/mixtures thereof.

8. The method of claim 1, wherein the purge gas is selected from the group consisting of nitrogen and argon.

* * * * *